United States Patent
Siemionow et al.

(10) Patent No.: US 11,263,772 B2
(45) Date of Patent: Mar. 1, 2022

(54) COMPUTER ASSISTED IDENTIFICATION OF APPROPRIATE ANATOMICAL STRUCTURE FOR MEDICAL DEVICE PLACEMENT DURING A SURGICAL PROCEDURE

(71) Applicant: Holo Surgical Inc., Chicago, IL (US)

(72) Inventors: Krzystof B. Siemionow, Chicago, IL (US); Cristian J. Luciano, Evergreen Park, IL (US); Dominik Gawel, Warsaw (PL); Marek Kraft, Warsaw (PL); Michal Trzmiel, Warsaw (PL); Michal Fularz, Warsaw (PL); Edwing Isaac Mejia Orozco, Warsaw (PL)

(73) Assignee: HOLO SURGICAL INC., Chicago, IL (US)

( * ) Notice: Subject to any disclaimer, the term of this patent is extended or adjusted under 35 U.S.C. 154(b) by 0 days.

(21) Appl. No.: 16/537,645

(22) Filed: Aug. 12, 2019

(65) Prior Publication Data

US 2020/0051274 A1    Feb. 13, 2020

(30) Foreign Application Priority Data

Aug. 10, 2018    (EP) .................................. 18188557

(51) Int. Cl.
*G06T 7/73*    (2017.01)
*A61B 34/10*    (2016.01)
(Continued)

(52) U.S. Cl.
CPC ............... *G06T 7/73* (2017.01); *A61B 34/10* (2016.02); *G06K 9/2054* (2013.01); *G06T 7/11* (2017.01);
(Continued)

(58) Field of Classification Search
CPC ...... G06T 7/73; G06T 7/62; G06T 7/11; G06T 2207/20081; G06T 2207/20084;
(Continued)

(56) References Cited

U.S. PATENT DOCUMENTS 6,405,072 B1    6/2002 Cosman
8,314,815 B2    11/2012 Navab et al.
(Continued)

FOREIGN PATENT DOCUMENTS

CN    106600568 A    4/2017
EP    2 922 025 A1    9/2015
(Continued)

OTHER PUBLICATIONS

Esfandiari, H., Newell, R., Anglin, C. et al. A deep learning framework for segmentation and pose estimation of pedicle screw implants based on C-arm fluoroscopy. Int J CARS 13, 1269-1282 (2018); Published: May 28, 2018 (Year: 2018).*
(Continued)

*Primary Examiner* — Bernard Krasnic

(57) ABSTRACT

A method for computer assisted identification of appropriate anatomical structure for placement of a medical device, comprising: receiving a 3D scan volume comprising set of medical scan images of a region of an anatomical structure where the medical device is to be placed; automatically processing the set of medical scan images to perform automatic segmentation of the anatomical structure; automatically determining a subsection of the 3D scan volume as a 3D ROI by combining the raw medical scan images and the obtained segmentation data; automatically processing the ROI to determine the preferred 3D position and orientation of the medical device to be placed with respect to the anatomical structure by identifying landmarks within the anatomical structure with a pre-trained prediction neural
(Continued)

network; automatically determining the preferred 3D position and orientation of the medical device to be placed with respect to the 3D scan volume of the anatomical structure.

21 Claims, 10 Drawing Sheets

(51) Int. Cl.
    *G06K 9/20*           (2006.01)
    *G06T 7/62*            (2017.01)
    *G06T 7/11*            (2017.01)

(52) U.S. Cl.
    CPC .......... *G06T 7/62* (2017.01); *A61B 2034/104* (2016.02); *A61B 2034/105* (2016.02); *A61B 2034/107* (2016.02); *G06K 2209/05* (2013.01); *G06T 2207/20081* (2013.01); *G06T 2207/20084* (2013.01); *G06T 2207/30021* (2013.01); *G06T 2207/30052* (2013.01)

(58) Field of Classification Search
    CPC ........... G06T 2207/30021; G06T 2207/30052; G06K 9/2054; G06K 2209/05; A61B 34/10; A61B 2034/104; A61B 2034/105; A61B 2034/107
    See application file for complete search history.

(56) References Cited

U.S. PATENT DOCUMENTS

| | | |
|---|---|---|
| 8,933,935 B2 | 1/2015 | Yang et al. |
| 9,289,267 B2 | 3/2016 | Sauer et al. |
| 9,532,848 B2 | 1/2017 | Amiot et al. |
| 9,949,700 B2 | 4/2018 | Razzaque et al. |
| 10,016,243 B2 | 7/2018 | Esterberg |
| 10,080,623 B2 | 9/2018 | Saito |
| 10,105,187 B2 | 10/2018 | Corndorf et al. |
| 10,646,283 B2 | 5/2020 | Johnson et al. |
| 10,646,285 B2 | 5/2020 | Siemionow et al. |
| 10,653,497 B2 | 5/2020 | Crawford et al. |
| 10,788,672 B2 | 9/2020 | Yadav et al. |
| 10,939,977 B2 | 3/2021 | Messinger et al. |
| 10,951,872 B2 | 3/2021 | Casas |
| 2002/0082498 A1 | 6/2002 | Wendt et al. |
| 2004/0047044 A1 | 3/2004 | Dalton |
| 2005/0190446 A1 | 9/2005 | Kuerz et al. |
| 2005/0289472 A1 | 12/2005 | Morita et al. |
| 2006/0176242 A1 | 8/2006 | Jaramaz et al. |
| 2008/0144773 A1 | 6/2008 | Bar-Zohar et al. |
| 2010/0328433 A1 | 12/2010 | Li |
| 2011/0229005 A1* | 9/2011 | Den Harder .......... G06K 9/3233 382/131 |
| 2011/0311113 A1 | 12/2011 | Baumgart |
| 2012/0314224 A1 | 12/2012 | Luellau |
| 2013/0226190 A1* | 8/2013 | Mckinnon .............. A61B 34/10 606/102 |
| 2015/0018622 A1 | 1/2015 | Tesar et al. |
| 2015/0125033 A1 | 5/2015 | Murphy et al. |
| 2015/0177598 A1 | 6/2015 | Mima et al. |
| 2015/0264339 A1 | 9/2015 | Riedel |
| 2016/0035139 A1 | 2/2016 | Fuchs et al. |
| 2016/0176242 A1 | 6/2016 | Nakamata |
| 2016/0187969 A1 | 6/2016 | Larsen et al. |
| 2016/0191887 A1 | 6/2016 | Casas |
| 2016/0278875 A1 | 9/2016 | Crawford et al. |
| 2016/0324580 A1 | 11/2016 | Esterberg |
| 2016/0328630 A1 | 11/2016 | Han et al. |
| 2017/0024903 A1 | 1/2017 | Razzaque |
| 2017/0042631 A1 | 2/2017 | Doo et al. |
| 2017/0056115 A1 | 3/2017 | Corndorf et al. |
| 2017/0084036 A1 | 3/2017 | Pheiffer et al. |
| 2017/0112575 A1* | 4/2017 | Li ............................. G06T 7/73 |
| 2017/0258526 A1 | 9/2017 | Lang |
| 2017/0323062 A1 | 11/2017 | Djajadiningrat et al. |
| 2017/0329402 A1 | 11/2017 | Riedel |
| 2017/0360395 A1 | 12/2017 | Razzaque |
| 2018/0012416 A1 | 1/2018 | Jones et al. |
| 2018/0042681 A1 | 2/2018 | Jagga |
| 2018/0078316 A1 | 3/2018 | Schaewe et al. |
| 2018/0082480 A1 | 3/2018 | White et al. |
| 2018/0140362 A1 | 5/2018 | Cali et al. |
| 2018/0174311 A1 | 6/2018 | Kluckner et al. |
| 2018/0185113 A1 | 7/2018 | Gregorson et al. |
| 2018/0225993 A1 | 8/2018 | Buras et al. |
| 2018/0271484 A1 | 9/2018 | Whisler |
| 2018/0303558 A1 | 10/2018 | Thomas |
| 2018/0311012 A1 | 11/2018 | Moctezuma et al. |
| 2019/0029757 A1 | 1/2019 | Roh et al. |
| 2019/0053851 A1 | 2/2019 | Siemionow et al. |
| 2019/0105009 A1 | 4/2019 | Siemionow et al. |
| 2019/0130575 A1 | 5/2019 | Chen et al. |
| 2019/0142519 A1 | 5/2019 | Siemionow et al. |
| 2019/0175285 A1 | 6/2019 | Siemionow et al. |
| 2019/0192230 A1 | 6/2019 | Siemionow et al. |
| 2019/0201106 A1 | 7/2019 | Siemionow et al. |
| 2019/0307513 A1 | 10/2019 | Leung et al. |
| 2019/0333626 A1 | 10/2019 | Mansi et al. |
| 2020/0151507 A1 | 5/2020 | Siemionow et al. |
| 2020/0229877 A1 | 7/2020 | Siemionow et al. |
| 2020/0327721 A1 | 10/2020 | Siemionow et al. |
| 2020/0410687 A1 | 12/2020 | Siemionow et al. |
| 2021/0267698 A1 | 9/2021 | Siemionow et al. |

FOREIGN PATENT DOCUMENTS

| | | | |
|---|---|---|---|
| EP | 3 151 736 A2 | 4/2017 | |
| EP | 3 221 809 A1 | 9/2017 | |
| EP | 3 361 979 A1 | 8/2018 | |
| EP | 3 432 263 A1 | 1/2019 | |
| GB | 2 536 650 A | 9/2016 | |
| WO | WO 2007/110820 A2 | 10/2007 | |
| WO | WO 2007/115826 A2 | 10/2007 | |
| WO | WO 2012/018560 A2 | 2/2012 | |
| WO | WO 2012/027574 A1 | 3/2012 | |
| WO | WO-2012027574 A1 * | 3/2012 | ............. A61B 34/10 |
| WO | WO 2015/058816 A1 | 4/2015 | |
| WO | WO 2016/010737 A2 | 1/2016 | |
| WO | WO 2016/078919 A1 | 5/2016 | |
| WO | WO 2017/066373 A1 | 4/2017 | |
| WO | WO 2017/091833 A1 | 6/2017 | |
| WO | 2018048575 A1 | 3/2018 | |
| WO | WO 2018/048575 A1 | 3/2018 | |
| WO | WO 2018/052966 A1 | 3/2018 | |
| WO | WO 2018/057564 A1 | 3/2018 | |
| WO | WO 2018/063528 A1 | 4/2018 | |
| WO | WO 2018/140415 A1 | 8/2018 | |
| WO | WO 2019/005722 A1 | 1/2019 | |
| WO | WO 2019/195926 A1 | 10/2019 | |

OTHER PUBLICATIONS

Non-Final Office Action dated Nov. 16, 2020 for U.S. Appl. No. 16/101,459, 43 pages.
Non-Final Office Action dated Sep. 16, 2019 for U.S. Appl. No. 16/059,061, 20 pages.
Non-Final Office Action dated Jul. 10, 2020 for U.S. Appl. No. 16/842,793, 23 pages.
Non-Final Office Action dated Oct. 28, 2020 for U.S. Appl. No. 16/186,549, 30 pages.
Extended European Search Report dated Oct. 25, 2017 for European Application No. 17186306.1, 14 pages.
Extended European Search Report dated Oct. 27, 2017 for European Application No. 17186307.9, 15 pages.
Extended European Search Report dated Feb. 16, 2018 for European Application No. 17195826.7, 8 pages.
Extended European Search Report dated Feb. 12, 2018 for European Application No. 17201224.7, 14 pages.
Extended European Search Report dated Feb. 27, 2018 for European Application No. 17206558.3, 13 pages.

(56) References Cited

OTHER PUBLICATIONS

Communication Pursuant to Article 94(3) dated Mar. 18, 2020 for European Application No. 17206558.3, 11 pages.
Extended European Search Report dated Apr. 17, 2019 for European Application No. 18211806.7, 8 pages.
Communication Pursuant to Article 94(3) dated Apr. 22, 2020 for European Application No. 18211806.7, 6 pages.
Extended European Search Report dated Jul. 5, 2018 for European Application No. 18150376.4, 10 pages.
Extended European Search Report dated Feb. 26, 2019 for European Application No. 18188557.5, 9 pages.
Extended European Search Report dated Feb. 1, 2019 for European Application No. 18205207.6, 9 pages.
Extended European Search Report dated Nov. 4, 2019 for European Application No. 19169136.9, 5 pages.
Extended European Search Report dated Oct. 23, 2019 for European Application No. 19179411.4, 8 pages.
Cernazanu-Glavan, C. et al., "Segmentation of Bone Structure in X-ray Images Using Conventional Neural Network," Advances in Electrical and Computer Engineering, 13(1):87-94 (2013); doi:10.4316/aece.2013.01015.
Chen, H. et al., "Low-dose CT denoising with convolutional neural network," 2017 IEEE 14th International Symposium on Biomedical Imaging (Apr. 2017), 4 pages; doi:10.1109/ISBI.2017.7950488.
Christ, P. F. et al., "Automatic Liver and Lesion Segmentation in CT Using Cascaded Fully Convolutional Neural Networks and 3D Conditional Random Fields," Oct. 7, 2016, 8 pages; arXiv:1610.02177v1.
Cramer, J., "Medical Image Segmentation and Design Tutorial with MevisLab," Apr. 27, 2016, retrieved on Jan. 26, 2018 from https://www.youtube.com/watch?v=PHf3Np37zTW, 1 page.
Egmont-Petersen, M. & Arts, T., "Recognition of radiopaque markers in X-ray images using a neural network as nonlinear filter," Pattern Recognition Letters, 20:521-533 (1999).
Fitzpatrick, J. M., "The role of registration in accurate surgical guidance," Proceedings of the Institute of Mechanical Engineering Medicine, Part H: Journal of Engineering in Medicine, 224(5):607-622 (2010); doi:10.1243/09544119JEIM589.
Gros, C. et al., "Automatic segmentation of the spinal cord and intramedullary multiple sclerosis lesions with convolutional neural networks," Neuroimage, 184:901-915 (2019).
Han, Z. et al., "Spine-GAN: Semantic segmentation of multiple spinal structures," Med Image Anal., 50:23-35 (2018); doi: 10.1016/j.media.2018.08.005. Epub Aug. 25, 2018.
Jiménez-Pastor, A. et al., "Automatic localization and identification of vertebrae in spine CT scans by combining Deep Learning with morphological image processing techniques," European Congress of Radiology (ECR) 2018, Mar. 4, 2018, retrieved from the Internet at: https://quibim.com/wp-content/uploads/2018/03/3_ECR2018_AJP, 30 pages.
Krinninger, M., "Ein System zur Endoskopführung in der HNO-Chirurgie," Dissertation, Mar. 15, 2011, XP055450605, Technischen Universität München, 151 pages.
Krinninger, M., "Ein System zur Endoskopführung in der HNO-Chirurgie," Dissertation, Mar. 15, 2011, XP055450605, Technischen Universität München; retrieved on Feb. 13, 2018 from https://mediatum.ub.tum.de/doc/998215/998215.pdf.—English Abstract, 1 page.
Krishnan, R. et al., "Automated Fiducial Marker Detection for Patient Registration in Image-Guided Neurosurgery," Computer Aided Surgery, 8(1): 17-23 (2003).
Liu, Yanfeng et al., "Human-Readable Fiducial Marker Classification using Convolutional Neural Networks," 2017 IEEE International Conference on Electro Information Technology (EIT), IEEE, May 14, 2017, 5 pages.
Lootus, M. et al., "Vertebrae Detection and Labelling in Lumbar MR Images," Jan. 1, 2014, 12 pages.
Mao, X.-J. et al., "Image Restoration Using Very Deep Convolutional Encoder-Decoder Networks with Symmetric Skip Connections," 29th Conference on Neural Information Processing Systems (NIPS 2016), Barcelona, Spain, 9 pages.
Shi, R. et al., "An Efficient Method for Segmentation of MRI Spine Images," IEEE/ICME International Conference on Complex Medical Engineering, Jun. 2007, 6 pages; doi:10.1109/ICCME.2007.4381830.
Song, Yuheng & Hao, Yan, "Image Segmentation Algorithms Overview," Jul. 7, 2017, retrieved from the Internet at: https://arxiv.org/ftp/arxiv/papers/1707/1707.02051, 6 pages.
Yang, D. et al., "Deep Image-to-Image Recurrent Network with Shape Basis Learning for Automatic Vertebra Labeling in Large-Scale 3D CT Volumes," Conference: International Conference on Medical Image Computing and Computer-Assisted Intervention, doi:10.1007/978-3-319-66179-7_57, Sep. 2017, 9 pages.
Non-Final Office Action dated Mar. 25, 2021 for U.S. Appl. No. 16/217,061, 25 pages.
Final Office Action dated Jun. 24, 2021 for U.S. Appl. No. 16/101,459, 40 pages.
Non-Final Office Action dated Apr. 28, 2021 for U.S. Appl. No. 16/217,073, 12 pages.
Non-Final Office Action dated Oct. 4, 2021 for U.S. Appl. No. 17/145,178, 22 pages.
Final Office Action dated Oct. 4, 2021 for U.S. Appl. No. 16/217,061, 68 pages.

\* cited by examiner

COMPUTER ASSISTED IDENTIFICATION OF APPROPRIATE ANATOMICAL STRUCTURE FOR MEDICAL DEVICE PLACEMENT DURING A SURGICAL PROCEDURE

TECHNICAL FIELD

The invention relates to computer assisted surgical navigation systems, in particular to a system and method for identifying appropriate anatomical structure for placement of a medical device, such as instrumentation or implant, during a surgical procedure, in particular related to neurological and general surgery procedures.

BACKGROUND

Image guided or computer assisted surgery is a surgical procedure where the surgeon uses trackable surgical instruments, combined with preoperative or intraoperative images (e.g., from computed tomography (CT) scanners), in order to provide the surgeon with surgical guidance during the procedure.

SUMMARY OF THE INVENTION

One of the disadvantages of known methods of image guided or computer assisted surgery is that they are not fully automatic. They require a specialized person to analyze the X-Ray, CT or NMR data and select a starting point for the procedure. Moreover they do not mention anything about the intraoperative CT allowing proper positioning during the surgery. In contrast, the invention, in certain embodiments, allows for fully automatic positioning and size determination in the 3D domain of the ongoing surgery thanks to usage of an intraoperative scanner and Artificial-Intelligence-based methods.

One aspect of the invention is a method for computer assisted identification of appropriate anatomical structure for placement of a medical device, comprising: receiving a 3D scan volume comprising set of medical scan images of a region of an anatomical structure where the medical device is to be placed; automatically processing the set of medical scan images to perform automatic segmentation of the anatomical structure; automatically determining a subsection of the 3D scan volume as a 3D region of interest by combining the raw medical scan images and the obtained segmentation data; automatically processing the ROI to determine the preferred 3D position and orientation of the medical device to be placed with respect to the anatomical structure by identifying landmarks within the anatomical structure with a pre-trained prediction neural network; automatically determining the preferred 3D position and orientation of the medical device to be placed with respect to the 3D scan volume of the anatomical structure.

The method may further comprise automatically identifying and storing the 3D position and orientation of the medical device placed by the surgeon in the anatomical structure during the surgical procedure, and using this information for further training of the prediction neural network in order to improve accuracy of the prediction neural network to subsequently identify the preferred positions and orientations to be suggested to the surgeon in successive surgical procedures.

The method may further comprise processing the scan images of the anatomical structures between the identified landmarks, and determining physical dimensions of the anatomical structures in the region of interest where the medical device is intended to be placed.

The method may further comprise determining preferred physical dimensions, the preferred physical dimensions including at least one of size, diameter and length, of the medical device to be placed depending on analyzed dimensions of the anatomical structure.

The received medical scan images may be collected from an intraoperative scanner.

The received medical scan images may be collected from a presurgical stationary scanner.

Another aspect of the invention is a computer-implemented system, comprising: at least one nontransitory processor-readable storage medium that stores at least one of processor-executable instructions or data; and at least one processor communicably coupled to at least one nontransitory processor-readable storage medium, wherein at least one processor is configured to perform the steps of the method as described herein.

These and other features, aspects and advantages of the invention will become better understood with reference to the following drawings, descriptions and claims.

BRIEF DESCRIPTION OF DRAWINGS

Various embodiments are herein described, by way of example only, with reference to the accompanying drawings, wherein:

FIG. 2E-1 shows 3 dimensional resizing of region of interest, in accordance with an embodiment of the invention;

FIG. 2E-2 shows 3 dimensional resizing of region of interest, in accordance with an embodiment of the invention;

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention.

The term "medical device" as used herein is understood to mean a surgical implant or an instrument, for example a catheter, instrument, a cannula, a needle, an anchor, a screw, a stent, a biomechanical device.

The invention is described below in detail with reference to an embodiment related to a neurological surgery, wherein a screw (as an example of a medical device) is placed, i.e. inserted, to a spine (as an example of an anatomical structure). A skilled person will realize that this embodiment can be extended to other applications as well, such as guidance for a medical device (e.g., instrumentation or implant) in other natural or artificial anatomical structures, for example blood vessels, biliary ducts, subthalamic nucleus, and components of solid organs like the heart (e.g., mitral valve), kidney (e.g., renal artery), and nerves (e.g., epidural space).

The automatic implant placement method as presented herein comprises two main procedures: a training procedure and a prediction procedure.

Figure 1:
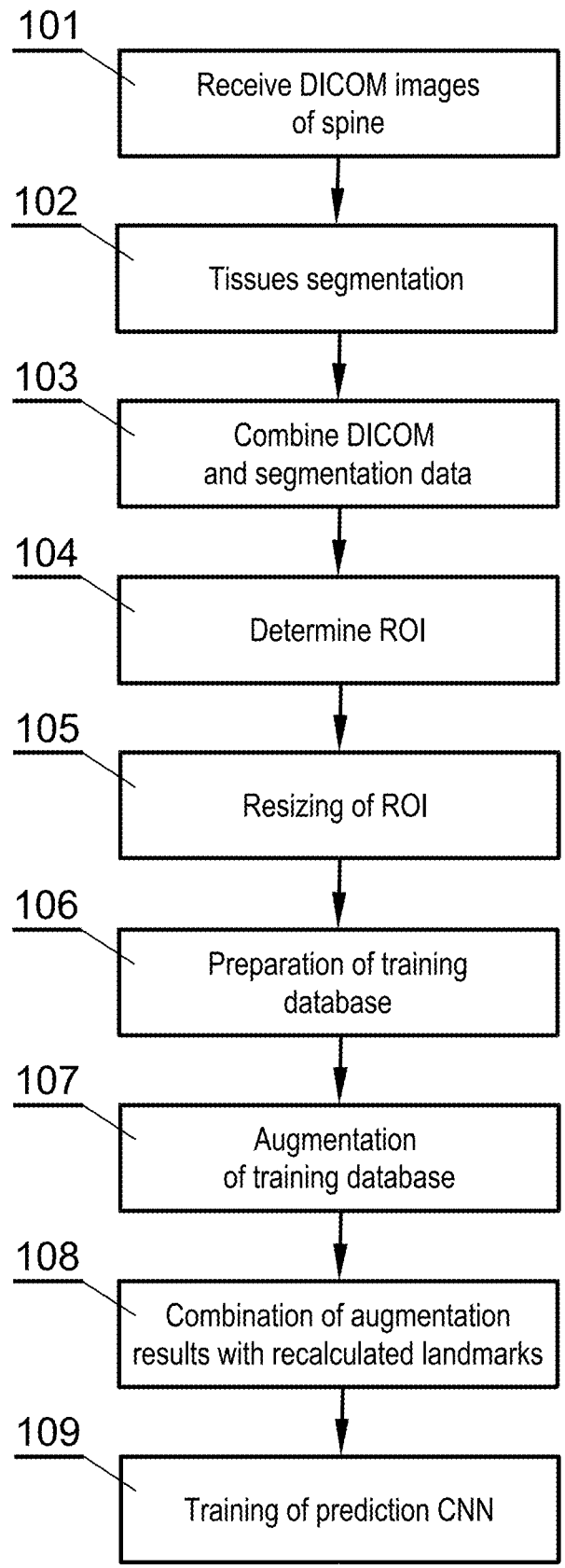
FIG. 1 shows an overview of a training procedure in accordance with an embodiment of the invention.
Figure 2A:
FIG. 2A shows an image used in the system during the training procedures, in accordance with an embodiment of the invention.
Figure 2B:
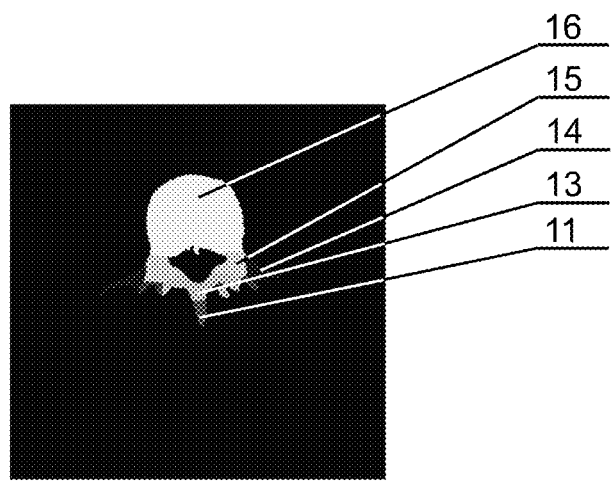
FIG. 2B shows an image used in a system during the training procedures, in accordance with an embodiment of the invention.
Figure 2C:
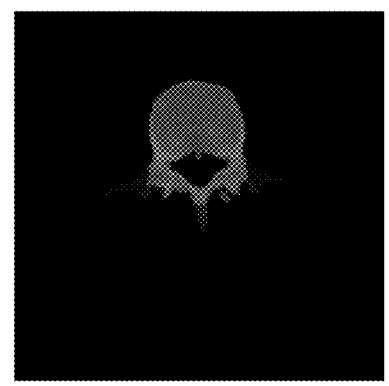
FIG. 2C shows an image used in the system during the training procedures, in accordance with an embodiment of the invention.
Figure 2D:
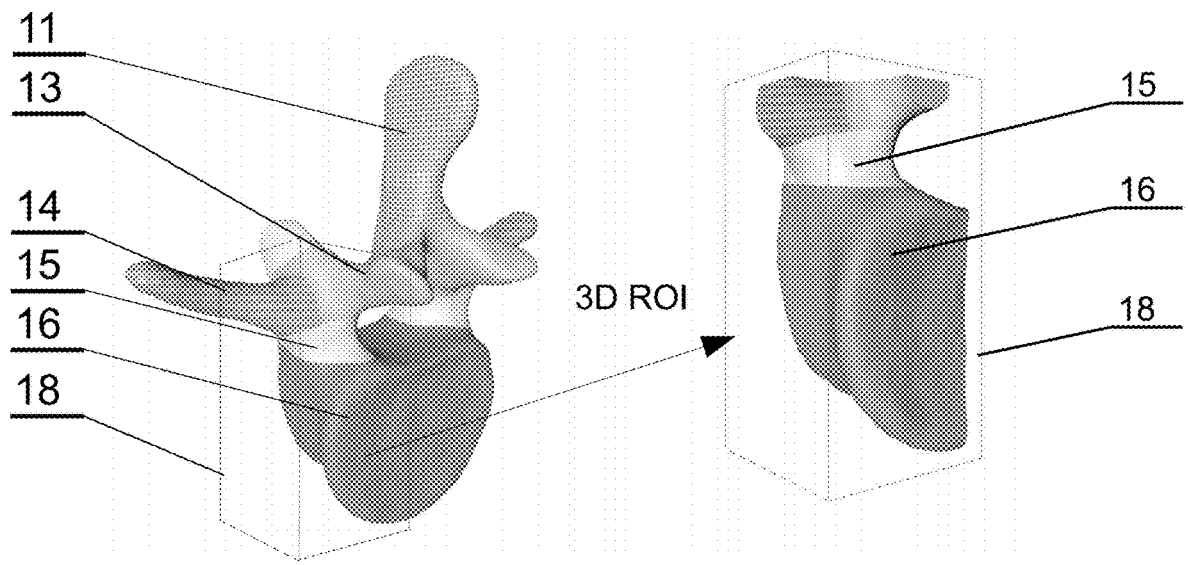
FIG. 2D shows region of interest used in the process, in accordance with an embodiment of the invention.
Figures 1, 2E:
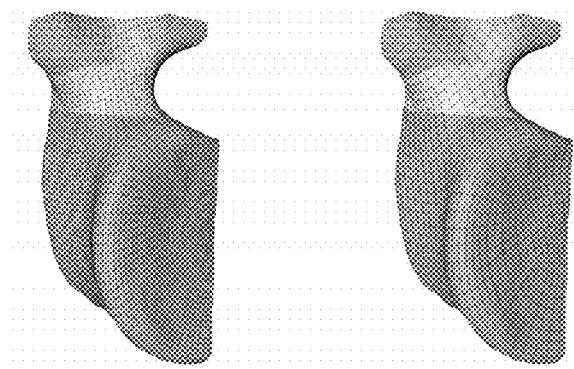
Figures 2, 2E:
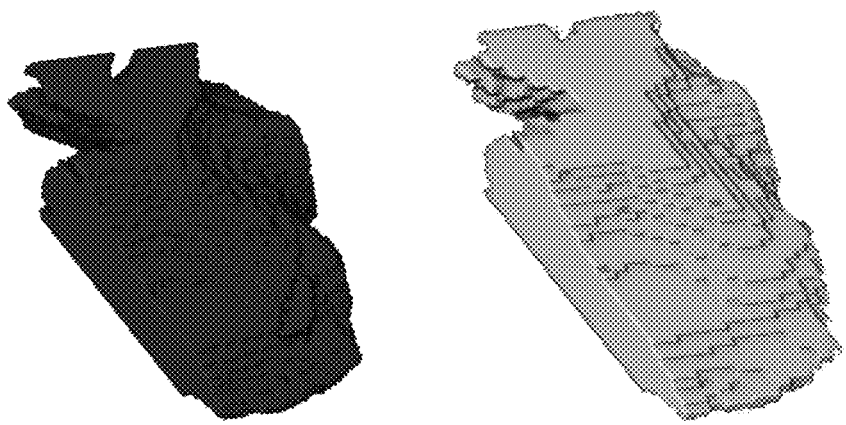

In certain embodiments, the training procedure, as presented in FIG. 1, comprises the following steps. First, in step 101, a set of DICOM (Digital Imaging and Communications in Medicine) images obtained with a preoperative or an intraoperative CT (Computed Tomography) or MRI (Magnetic Resonance Imaging) representing consecutive slices with visible tissues is received (such as one slice shown in FIG. 2A). Next, the received images are processed in step 102 to perform automatic segmentation of tissues, such as to determine separate areas corresponding to different tissues, such as vertebral body 16, pedicles 15, transverse processes 14 and/or spinous process 11, as shown in FIG. 2B. For example, this can be done by employing a method for segmentation of images disclosed in Applicant's European patent application EP17195826 filed Oct. 10, 2017 and published as EP 3 470 006 A1 on Apr. 17, 2019. Then, in step 103, the information obtained from DICOM images and the segmentation results is merged to obtain combined image comprising information about the tissue appearance and its classification (including assignment of structure parts to classes corresponding to different anatomy parts), for example in a form of a color-coded DICOM image, as shown in FIG. 2C. Alternatively, separate DICOM (FIG. 2A) and segmentation (FIG. 2B) images can be processed instead of the combined image. Next, in step 104, from the set of slice images a 3D region of interest (ROI) 18 is determined, that contains a volume of each pedicle 15 with a part of adjacent vertebral body 16 and surrounding tissues such as lamina 13, transverse process 14 and others, as shown in FIG. 2D. Then, in step 105, the 3D resizing of the determined ROI 18 is performed to achieve the same size of all ROI's stacked in the 3D matrices, each containing information about voxel distribution along X, Y and Z axes and the appearance and classification information data for each voxel, such as shown in FIG. 2E-1 or 2E-2. In other words, the voxels are small cuboidal volumes resembling points having 3D coordinates and a radiodensity value and classification assigned.

Figure 2F:
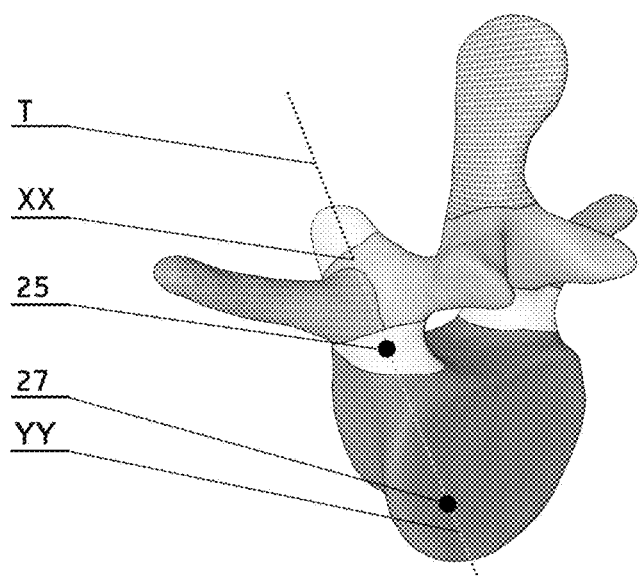
FIG. 2F shows exemplary characteristic features localization, in accordance with an embodiment of the invention.

Next, in step 106, a training database is prepared manually, that comprises the previously determined ROIs and manually landmarked characteristic features corresponding to pedicle center 25 and screw tip 27 (or other anatomical structure and device points), such as shown in FIG. 2F.

Figure 2G:
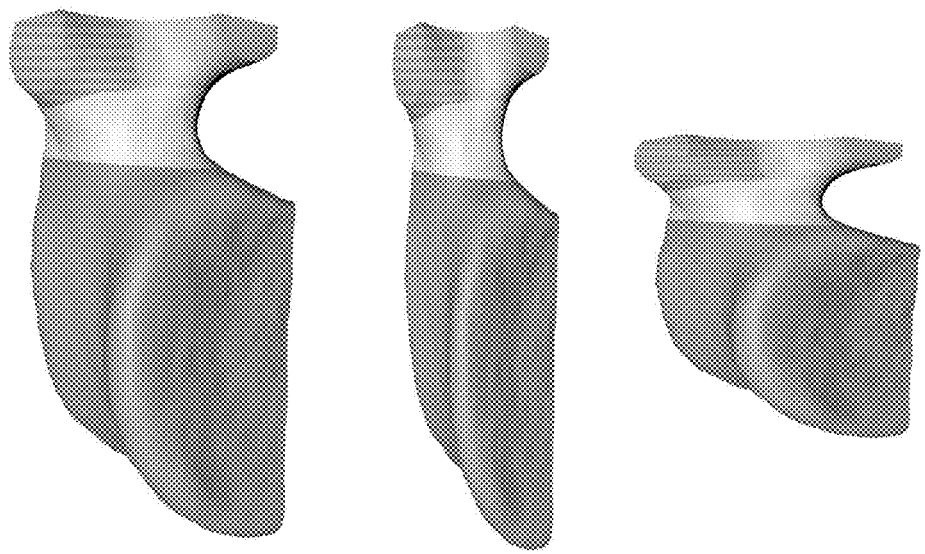
FIG. 2G shows exemplary results of artificial training database augmentation, in accordance with an embodiment of the invention.

Next, in step 107, the training database is augmented, for example with the use of a 3D generic geometrical transformation and resizing with random dense 3D grid deformations, as shown in FIG. 2G. Data augmentation is performed on the images to make the training set more diverse. The foregoing transformations are remapping the voxels positions in a 3D ROI 18 based on a randomly warped artificial grid assigned to the ROI 18 volume. A new set of voxel positions is calculated artificially warping the 3D tissue shape and appearance. Simultaneously, the information about the tissue classification is warped to match the new tissue shape and the manually determined landmarks positions 25, 27 are recalculated in the same manner During the process, the value of each voxel, containing information about the tissue appearance, is recalculated in regards to its new position in ROI 18 with use of an interpolation algorithm (for example bicubic, polynomial, spline, nearest neighbor, or any other interpolation algorithm) over the 3D voxel neighborhood.

Next, in step 108, the obtained artificial database augmentation results are combined with the automatically recalculated landmarks, corresponding to the artificially augmented pedicle centers 25 and screw tips 27 (or other anatomical structure and device points), into a single database interpretable by a neural network.

Figure 4:
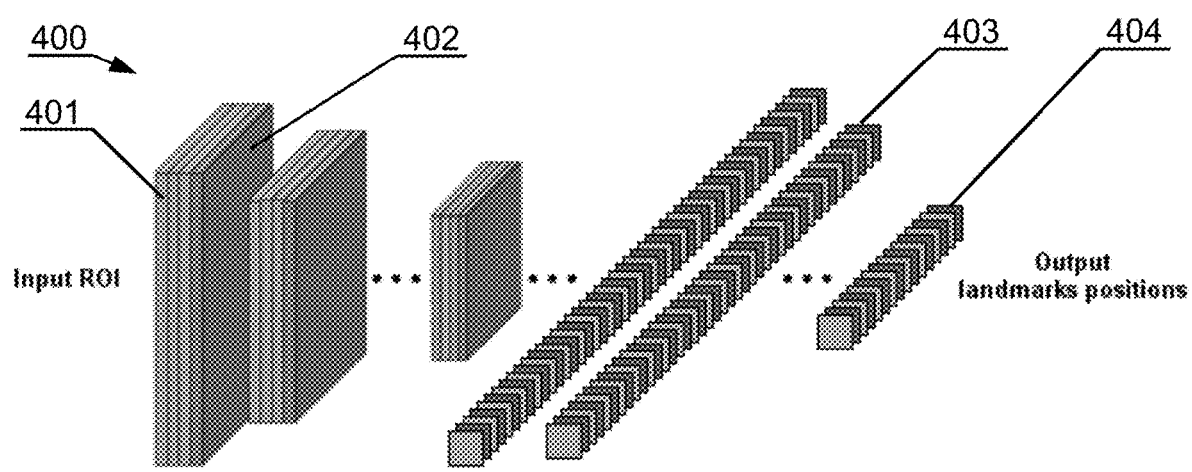
FIG. 4 shows a prediction CNN architecture, in accordance with an embodiment of the invention.
Figure 5:
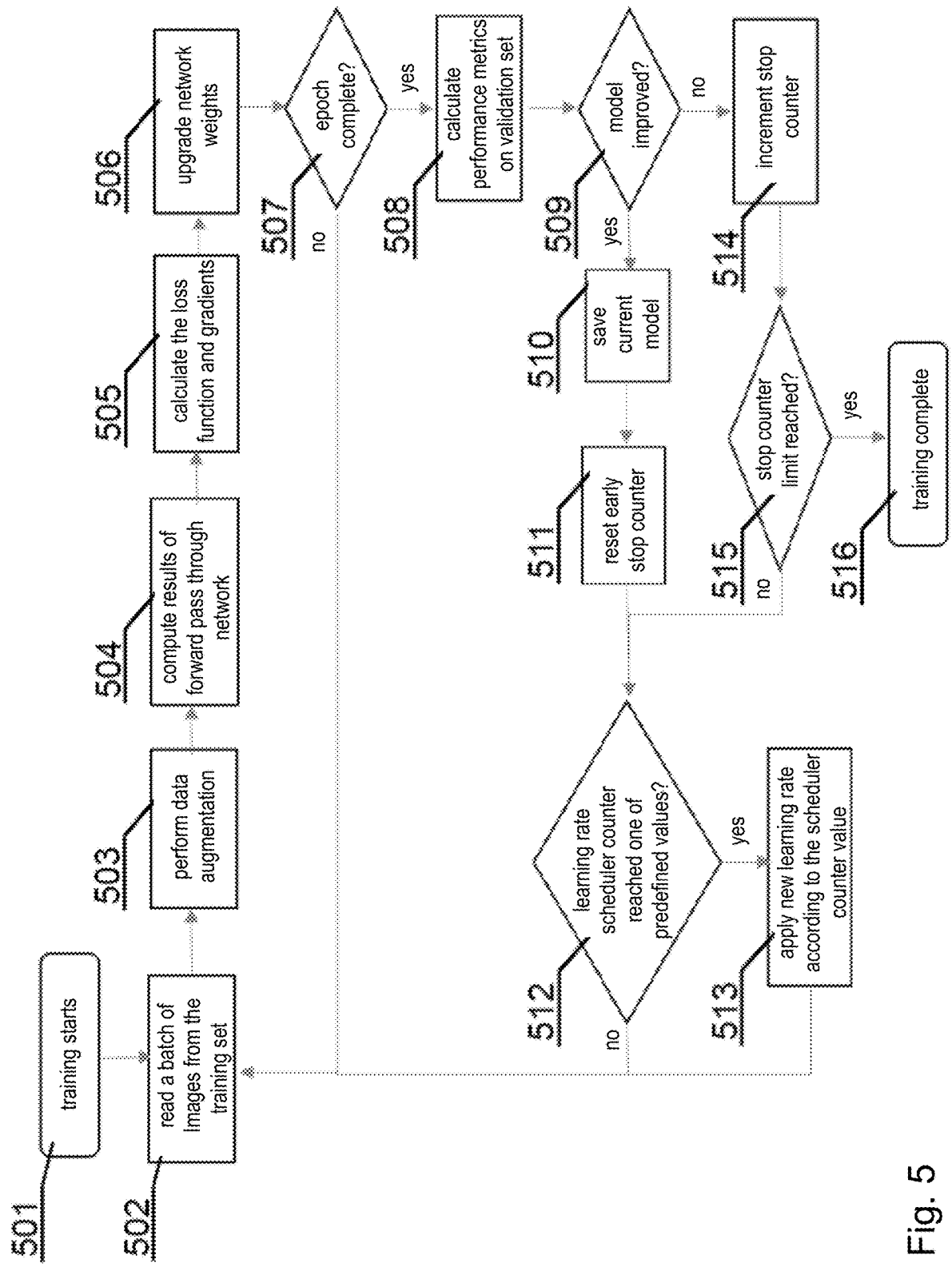
FIG. 5 shows a flowchart of a training process for the prediction CNN, in accordance with an embodiment of the invention.

Then, in step 109, the placement prediction model is trained with a neural network. In certain embodiments, a network with a plurality of layers is used, specifically a combination of convolutional and fully connected layers with ReLU activation functions or any other non-linear or linear activation functions. For example, a network such as shown in FIG. 4, according to a process such as shown in FIG. 5, can be used.

The training database may also comprise data from actually performed surgical procedures. The system may automatically identify and store the 3D position and orientation of the medical device actually inserted by the surgeon in the anatomical structure during the surgical procedure, for further training the prediction neural network (400) in order to improve its performance to subsequently identify the preferred positions and orientations. Therefore, the system may operate like a closed feedback loop.

Figure 3:
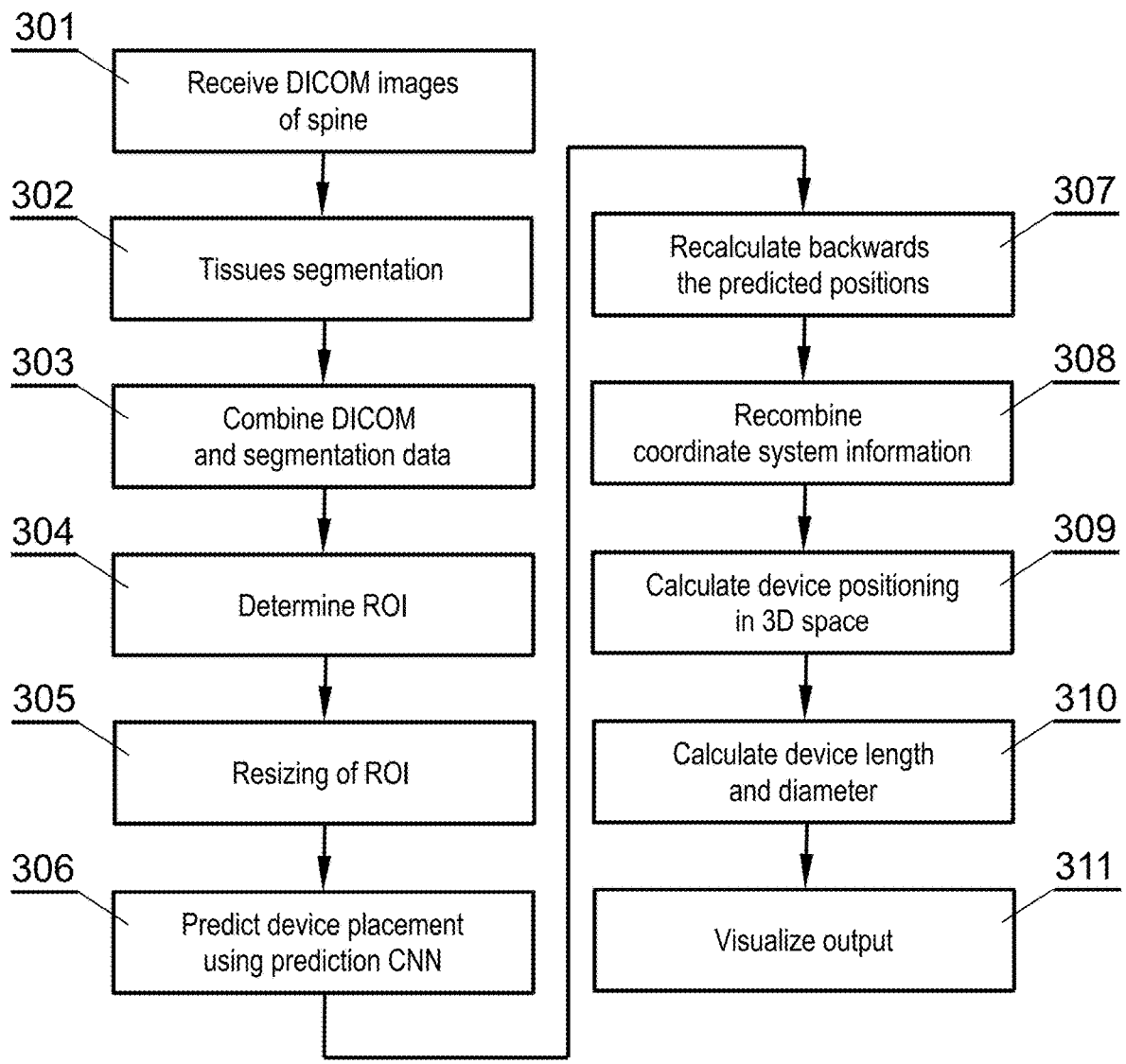
FIG. 3 shows an overview of a prediction procedure, in accordance with an embodiment of the invention.

In certain embodiments, the prediction procedure, as presented in FIG. 3, comprises the following steps. First, in step 301, a 3D scan volume is received, comprising a set of DICOM (Digital Imaging and Communications in Medicine) images of a region of the anatomical structure where the medical device is to be placed. The 3D scan volume can be obtained with a preoperative or an intraoperative CT (Computed Tomography) or MRI (Magnetic Resonance Imaging). The set of DICOMs representing consecutive slices of a spine is received (such as one slice shown in FIG. 2A). Next, the received images are processed in step 302 to perform automatic segmentation of tissues of the anatomical structure, such as to determine separate areas corresponding to different tissues, such as vertebral body 16, pedicles 15, transverse processes 14, lamina 13 and/or spinous process 11, as shown in FIG. 2B. For example, this can be done by employing a method for segmentation of images disclosed in Applicant's European patent application EP17195826 filed Oct. 10, 2017 and published as EP 3 470 006 A1 on Apr. 17, 2019, incorporated herein by reference in its entirety. Then, in step 303, the information obtained from DICOM images and the segmentation results is merged to obtain combined image comprising information about the tissue appearance and its classification, for example in a form of a color-coded DICOM image, as shown in FIG. 2C. Alternatively, separate DICOM (FIG. 2A) and segmentation (FIG. 2B) images can be processed instead of the combined image. Next, in step 304, from the 3D scan volume a 3D region of interest (ROI) 18 is automatically determined. For example, the ROI 18 may contain a volume of each pedicle 15 with a part of adjacent vertebral body and surrounding tissues, as shown in FIG. 2D. Then, in step 305, the 3D resizing of the determined ROI 18 is performed to achieve the same size of all ROI's stacked in the 3D matrices. Each 3D matrix contains information about voxel distribution along X, Y and Z axes with bone density and classification information data for each voxel, such as shown in FIG. 2E-1 or 2E-2. Therefore, steps 301-305 are performed in a way similar to steps 101-105 of the training procedure of FIG. 1.

Figure 6:
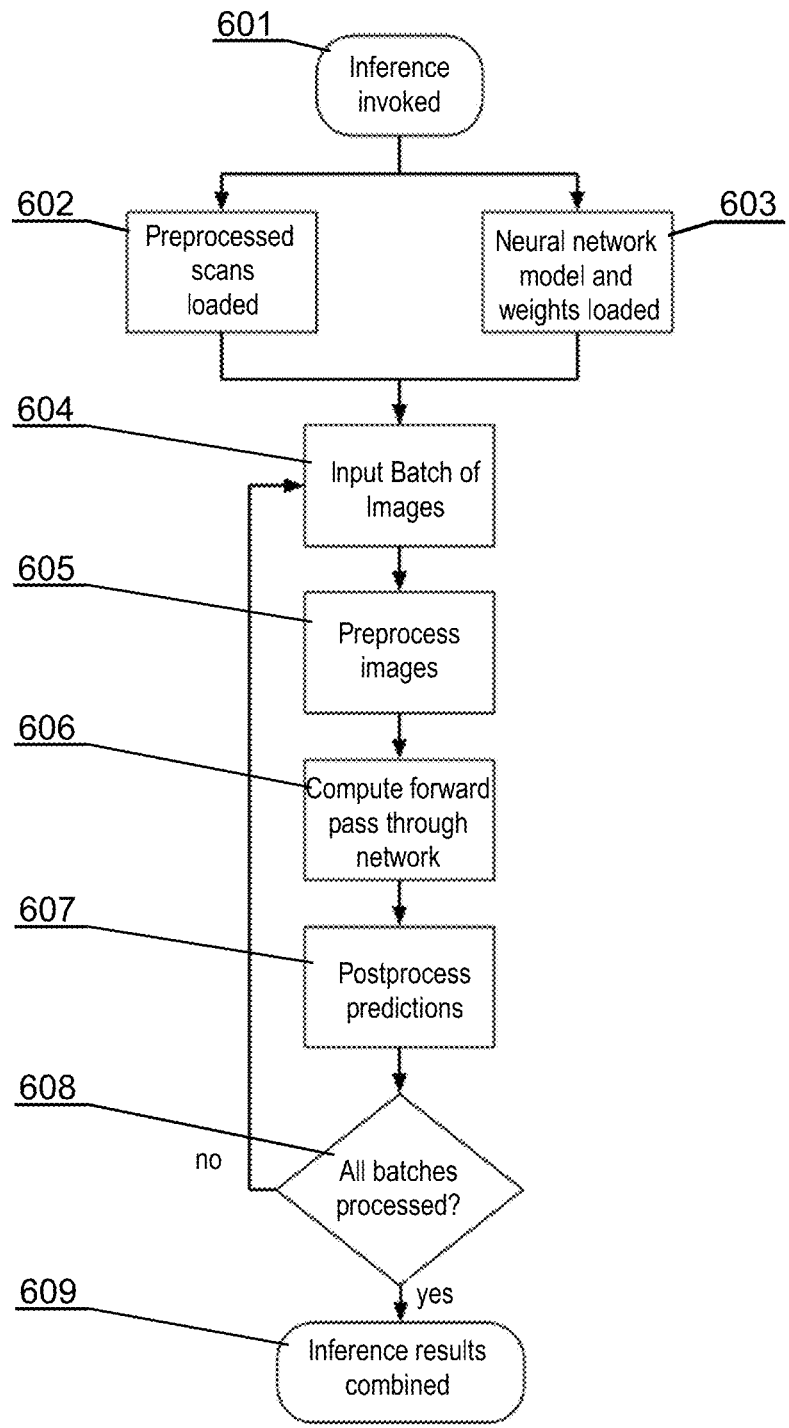
FIG. 6 shows a flowchart of an inference process for the prediction CNN, in accordance with an embodiment of the invention.

Next, in step 306, the preferred placement is predicted automatically by processing the resized ROI to determine the preferred 3D position and orientation of the medical device to be placed with respect to the anatomical structure, by means of the pretrained prediction CNN 400, according to the prediction process presented in FIG. 6. The prediction CNN 400 is configured to identify landmarks within the anatomical structure, such as pedicle center 25 and screw tip 27.

Next, in step 307, the predicted screw tip 25 and pedicle center 27 (or other anatomical structure and device landmarks) positions within the ROI are backward recalculated to meet the original ROI size and positions from input DICOM dataset to recreate and ensure a correct placement in original volume.

In step 308 the information about the global coordinate system (ROI position in the DICOM dataset) and local ROI coordinate system (predicted screw tip and pedicle center positions inside the ROI) is recombined.

Then, in step 309, the preferred device positioning in the 3D space is calculated, based on two landmarks corresponding to pedicle center 25 and screw tip 27, as shown in FIG. 2F.

Anatomical knowledge and preferred device positioning allow for the calculation of a preferred device's physical dimensions, for example screw positioning in the vertebra. With the semantic/anatomical segmentation results and pedicle center 25 location available, in step 310, automated computation of device physical dimensions, such as the diameter, is possible. Proceeding in the coronal direction, forward and backward from the pedicle center landmark 25 along the pedicle, the slice for which the inscribed circle diameter will be the smallest can easily be found. A fraction of this diameter corresponds directly to the inserted device maximum allowed diameter with a necessary safety margin that can be easily defined by the user of the system.

Enabling selection of a specific element in the available series of types also requires determination of device physical dimensions such as the length. This too can be easily computed automatically using the device insertion trajectory information provided by the neural network. The line going through the estimated landmarks (bone anchor tip 27, pedicle center 25) represents the trajectory of the device, which can be expressed as a 3D path, in the case of 2 landmarks it will be line model. Given the trajectory of a medical device to be inserted and an anatomical structure being a target, the entry and exit points could be calculated using automated 3D image analysis. For example, given the 3D line model and a 3D shell of the shape of the anatomical part being a target of device insertion extracted using morphological gradient in 3D (a single voxel thick surface of all solids in the volume), the entry and exit points of the trajectory are located at the two shell voxels (XX, YY) that are closest to the line (trajectory T) at each end, for example such as shown in FIG. 2F.

Figure 2H:
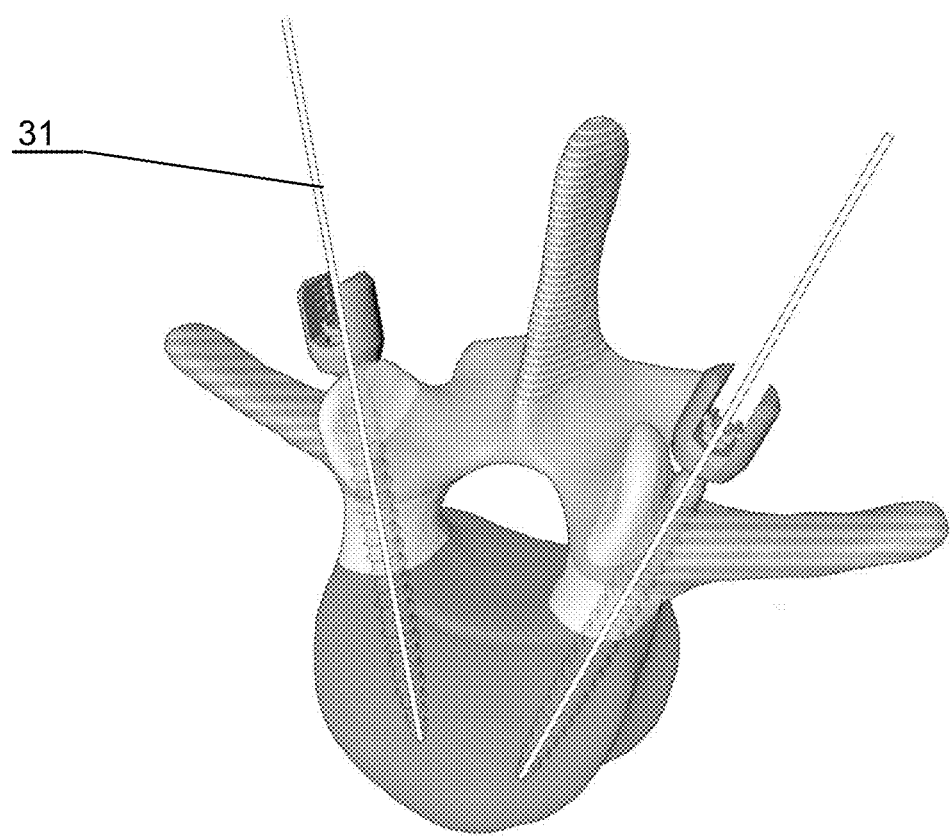
FIG. 2H shows exemplary final implant localization, in accordance with an embodiment of the invention.

Next, in step 311, the output is visualized, for example such as shown in FIG. 2H, including the device 31 to be inserted.

FIG. 4 shows a convolutional neural network (CNN) architecture 400, hereinafter called the prediction CNN, which is utilized in certain embodiments of the method of the invention for prediction of device placement. The network performs device localization task using at least one input as a 3D information about the appearance (radiodensity) and the classification for each voxel in a 3D ROI.

The left side of the network is a contracting path, which includes convolution layers 401 and pooling layers 402, and the right side is a regression path which includes fully connected layers 403 and the output layer 404.

One or more 3D ROI's can be presented to the input layer of the network to learn reasoning from the data.

The convolution layers 401 can be of a standard kind, the dilated kind, or a combination thereof, with ReLU, leaky ReLU or any other kind of activation function attached.

The fully connected layers 403 can have Linear, ReLU or any other kind of activation function attached.

The output layer 404 also denotes the fully connected layer with the loss function, for example the loss function can be implemented as mean squared error or another metric.

The architecture is general, in the sense that adopting it to ROI's of different size is possible by adjusting the size (resolution) of the layers. The number of layers and number of filters within a layer is also subject to change, depending on the requirements of the application, for example as presented in Applicant's European patent application EP17195826.

The final layer for the device placement defines the preferred device position and orientation along X, Y and Z axes in 3D ROI. Prediction is based on the model trained from the manually prepared examples during the training process, for example in case of screw insertion, preferred position of the pedicle center 25 and screw tip 27.

FIG. 5 shows a flowchart of a training process, in accordance with certain embodiments, which can be used to train the prediction CNN 400. The objective of the training for the prediction CNN 400 is to tune the parameters of the prediction CNN 400 such that the network is able to predict preferred guidance for the device.

The training database may be separated into a training set used to train the model, a validation set used to quantify the quality of the model, and a test set.

The training starts at 501. At 502, batches of training ROI's are read from the training set, one batch at a time.

At 503 the ROI's can be additionally augmented. Data augmentation is performed on these ROI's to make the training set more diverse. The input/output data is subjected to the combination of transformations from the following set: rotation, scaling, movement, horizontal flip, additive noise of Gaussian and/or Poisson distribution and Gaussian blur, volumetric grid deformation, etc. or could be augmented with the use of generative algorithm such as Generative Adversarial Networks for example.

At 504, the ROI's are then passed through the layers of the CNN in a standard forward pass. The forward pass returns the results, which are then used to calculate at 505 the value of the loss function—the difference between the desired and the computed outputs. The difference can be expressed using a similarity metric (e.g., mean squared error, mean average error or another metric).

At 506, weights are updated as per the specified optimizer and optimizer learning rate using Gradient Descent methods (e.g., Stochastic Gradient Descent, Adam, Nadam, Adagrad, Adadelta, RMSprop).

The loss is also back-propagated through the network, and the gradients are computed. Based on the gradient values, the network's weights are updated. The process (beginning with the ROI's batch read) is repeated continuously until the end of the training session is reached at 507.

Then, at 508, the performance metrics are calculated using a validation dataset—which is not explicitly used in training set. This is done in order to check at 509 whether or not the model has improved. If it is not the case, the early stop counter is incremented at 514 and it is checked at 515 if its value has reached a predefined number of epochs. If so, then the training process is complete at 516, since the model has not improved for many sessions now.

If the model has improved, the model is saved at 510 for further use and the early stop counter is reset at 511. As the final step in a session, learning rate scheduling can be applied. The sessions at which the rate is to be changed are predefined. Once one of the session numbers is reached at 512, the learning rate is set to one associated with this specific session number at 513.

Once the training is complete, the network can be used for inference (i.e., utilizing a trained model for prediction on new data).

FIG. 6 shows a flowchart of an inference process for the prediction CNN 400 in accordance with certain embodiments of the invention.

After inference is invoked at 601, a set of ROI's is loaded at 602 and the prediction CNN 400 and its weights are loaded at 603.

At 604, one batch of ROI's at a time is processed by the inference server.

At 605, the images can be preprocessed (e.g., normalized)

At 606, a forward pass through the prediction CNN 400 is computed.

At 607, a postprocess prediction is done.

At 608, if not all batches have been processed, a new batch is added to the processing pipeline until inference has been performed on all input ROI's.

Finally, at 609, the inference results are saved and can be recalculated to provide an output in a form of preferred device position.

Figure 7:
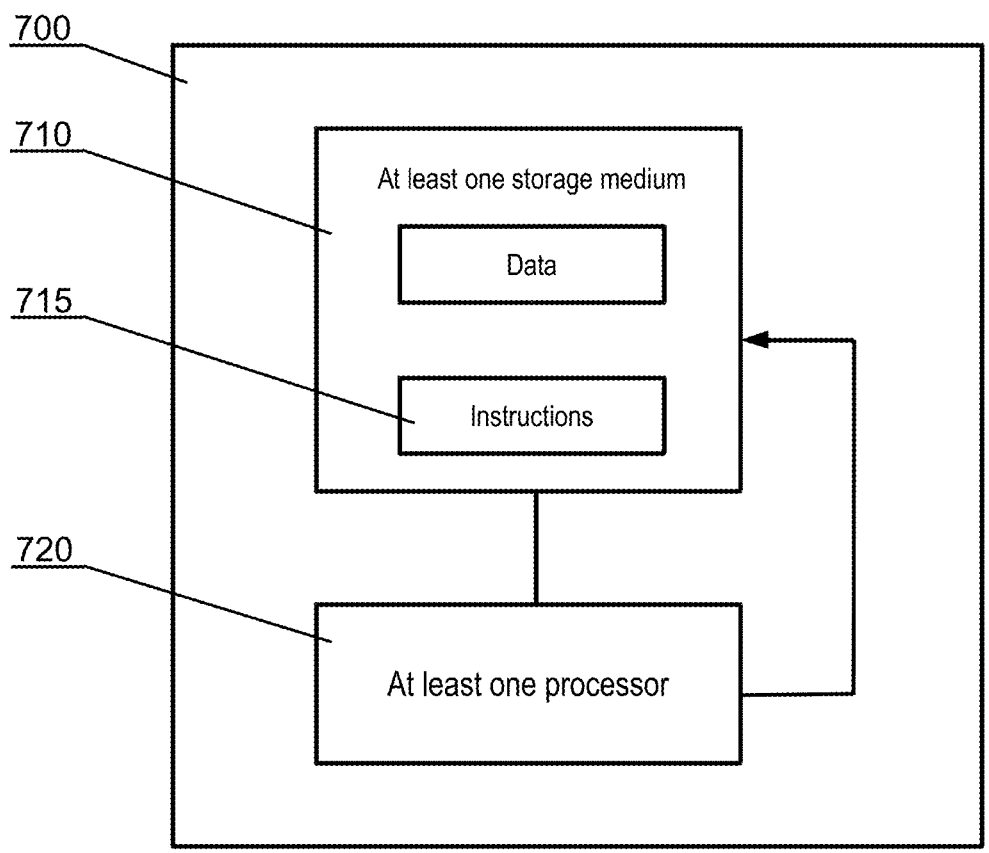
FIG. 7 shows the structure of a computer system for implementing the method of FIG. 1, in accordance with an embodiment of the invention.

The functionality described herein can be implemented in a computer system 700, such as shown in FIG. 7. The system 700 may include at least one nontransitory processor-readable storage medium 710 that stores at least one of processor-executable instructions 715 or data; and at least one processor 720 communicably coupled to the at least one nontransitory processor-readable storage medium 710. The at least one processor 720 may be configured to (by executing the instructions 715) perform the procedure of FIG. 1.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A method for computer assisted identification of an anatomical structure for placement of a medical device, the method comprising:

receiving a three-dimensional (3D) scan volume comprising a set of medical scan images of a region of the anatomical structure where the medical device is yet to be placed;

processing the set of medical scan images to obtain segmentation data of the anatomical structure that identifies different anatomical parts of the anatomical structure;

determining a subsection of the 3D scan volume as a 3D region of interest (ROI) where the medical device is yet to be placed, the 3D ROI including image data from the set of medical scan images and segmentation data associated with the subsection of the 3D scan volume;

processing the 3D ROI with a prediction neural network model to identify landmarks associated with a set of anatomical parts within the anatomical structure for the placement of the medical device; and determining preferred 3D positioning, orientation, and dimensions of the medical device yet to be placed with respect to the 3D scan volume of the anatomical structure based on the landmarks.

2. The method according to claim 1, further comprising:

identifying and storing, after the medical device has been placed by a surgeon within the anatomical structure during the surgical procedure, actual 3D positioning and orientation of the medical device; and training the prediction neural network using the actual 3D positioning and orientation of the medical device to improve accuracy of the prediction neural network to subsequently identify preferred positioning, orientation, and dimensions of the medical device to be suggested to the surgeon in successive surgical procedures.

3. The method according to claim 1, further comprising:

processing the medical scan images of the set of medical scan images of the set of anatomical parts associated with the landmarks; and determining physical dimensions of the set of anatomical parts in the 3D ROI for the placement of the medical device.

4. The method according to claim 3, wherein determining the preferred 3D dimensions includes determining at least one of size, diameter, or length of the medical device to be placed based on the physical dimensions of the set of anatomical parts.

5. The method according to claim 1, wherein the set of medical scan images is collected using an intraoperative scanner.

6. The method according to claim 1, wherein the set of medical scan images is collected using a presurgical stationary scanner.

7. A computer-implemented system for computer assisted identification of an anatomical structure for placement of a medical device, comprising:

at least one nontransitory processor-readable storage medium that stores at least one of processor-executable instructions or data; and at least one processor communicably coupled to the at least one nontransitory processor-readable storage medium, wherein the at least one processor is configured to:

process a set of medical scan images to obtain segmentation data of the anatomical structure that identifies different anatomical parts of the anatomical structure, the set of medical scan images being from a three-dimensional (3D) scan volume of a region of the anatomical structure where the medical device is yet to be placed;

determine a subsection of the 3D scan volume as a 3D region of interest (ROI) where the medical device is yet to be placed, the 3D ROI including image data from the set of medical scan images and segmentation data associated with the subsection of the 3D scan volume;

process the 3D ROI with a prediction neural network model to identify landmarks associated with a set of anatomical parts within the anatomical structure for the placement of the medical device; and determine preferred 3D positioning, orientation, and dimensions of the medical device yet to be placed with respect to the 3D scan volume of the anatomical structure based on the landmarks.

8. The method according to claim 1, further comprising:
resizing the 3D ROI such that a ROI in each medical scan image from the set of medical scan images stacked in the subsection of the 3D scan volume has a same size,
the processing of the 3D ROI with the prediction neural network model occurring after the resizing of the 3D ROI.

9. The method according to claim 8, further comprising:
reverting, after the processing of the 3D ROI with the prediction neural network model, the size of the ROI in each medical scan image from the set of medical scan images stacked in the subsection of the 3D scan volume to determine a position of the identified landmarks within the 3D ROI.

10. The method according to claim 1, further comprising:
combining, after the processing of the 3D ROI with the prediction neural network model, coordinate information indicative of a position of the landmarks within a local coordinate system of the 3D ROI with coordinate information indicative of a position of the 3D ROI within a global coordinate system of the 3D scan volume, and
the determining the preferred 3D positioning, orientation, and dimensions of the medical device is based on the combined coordinate information.

11. The method according to claim 1, further comprising:
training the prediction neural network model using a training set including previously determined ROIs with marked characteristic features associated with the landmarks.

12. The method according to claim 11, wherein the landmarks include at least one of a pedicle center or a tip of the medical device.

13. The method according to claim 11, further comprising validating a quality of the prediction neural network model using a validation set including 3D scan volumes of regions of anatomical structures.

14. The method according to claim 11, further comprising augmenting the training set by transforming the previously determined ROIs using one or more of: rotation, scaling, movement, horizontal flip, additive noise of Gaussian or Poisson distributions and Gaussian blur, volumetric grid deformation, or a generative algorithm,
and the predictive neural network model being trained using the augmented training set.

15. The method according to claim 1, wherein the processing the 3D ROI with the prediction neural network model includes processing the 3D ROI through a set of layers of the prediction neural network model in a standard forward pass to obtain outputs of the prediction neural network model.

16. The method according to claim 15, wherein the processing the 3D ROI further comprises calculating a value of a loss function associated with the prediction neural network model based on the outputs of the standard forward pass.

17. The method according to claim 16, wherein the processing the 3D ROI further comprises updating a set of weights of the prediction neural network model by backward-propagating the value of the loss function through the set of layers of the prediction neural network model.

18. The method according to claim 14, wherein the augmenting the training set includes recalculating a position of the landmarks in each of the transformed 3D ROIs.

19. The method according to claim 1, further comprising backward recalculating one or more of the preferred 3D positioning, orientation, and dimensions of the medical device yet to be placed, 3D scan volume of the anatomical structure, and the landmarks.

20. The method according to claim 1, wherein the preferred 3D positioning, orientation, and dimensions of the medical device yet to be placed is based on two of the landmarks.

21. The method according to claim 1, further comprising visualizing the preferred 3D positioning, orientation, and dimensions of the medical device yet to be placed with respect to the anatomical structure.

* * * * *